US00PP08656P

United States Patent [19]

De Meyer

[11] Patent Number: Plant 8,656

[45] Date of Patent: Mar. 22, 1994

[54] GUZMANIA PLANT NAMED TRIUMPH

[75] Inventor: Hendrik De Meyer, Destelbergen, Belgium

[73] Assignee: H. De Meyer - De Rouck, Laarne, Belgium

[21] Appl. No.: 999,201

[22] Filed: Dec. 31, 1992

[51] Int. Cl.[5] ..... A01H 5/00

[52] U.S. Cl. ..... Plt./88.8

[58] Field of Search ..... Plt. 88.1, 88.8

*Primary Examiner*—James R. Feyrer

*Attorney, Agent, or Firm*—Foley & Lardner

[57] ABSTRACT

A new and distinct cultivar of Guzmania plant named Triumph, characterized by its bright red bracts which are shaped in the form of a cone, green lower leaves which contrast nicely with the bracts, long lasting inflorescence, and well formed leaf sheaths closely linked at the base.

2 Drawing Sheets

The present invention comprises a new and distinct cultivar of *Guzmania squarrosa*×*minor*, referred to by the cultivar name Triumph. The genus Guzmania is within the family Bromeliaceae.

Triumph is a product of a planned breeding program conducted in Laarne, Belgium. The program evolved from the importation by the inventor of seeds of several different cultivars of *Guzmania squarrosa* from Ecuador. When grown out to flower, several plants were selected for their beautiful flowers, and were subsequently crossed with cultivars of the species Guzmania minor.

Triumph was originated by the inventor Hendrik De Meyer from a hybridization made in the program in Laarne, Belgium. The female parent was an unnamed *Guzmania minor* cultivar. The male parent of Triumph was an unnamed *Guzmania squarrosa* cultivar.

Triumph was discovered and selected by the inventor after flowering in early 1991. The new cultivar was thereafter asexually reproduced from offshoots under the supervision of the inventor in a controlled environment in Laarne, Belgium. The offshoots were rooted, with the resulting plantlets being detached from the mother plant and potted up in an appropriate growing mixture.

Horticultural examination of plants so propagated has demonstrated that the combination of characteristics as herein disclosed for Triumph are firmly fixed and retained through successive generations of asexual reproduction, which can be effected by offshoots as described, or by known tissue culture techniques.

Although asexual or vegetative propagation is an effective and preferred replication technique, it has been discovered that both parents have a high degree of homozygosity so that the progeny of the cross were and continue to be phenotpyically similar. The new cultivar is not fertile and; cannot be propagated from its own seed.

Triumph has not been observed under all possible environmental conditions. The phenotype may vary significantly when grown under different conditions of temperature, light, and other determining factors, without, however, any variation in genotype. The following observations, measurements and comparisons describe plants grown in Laarne, Belgium under greenhouse conditions which approximate those generally used in commercial practice.

The following traits have been repeatedly observed and are determined to be basic characteristics of Triumph which in combination distinguish this Guzmania as a new and distinct cultivar:

1. Triumph has bright red bracts which together (25 bracts) constitute a cone. The bracts at the bottom of the flower-shaft have a width of about 4.5 cm and a length of 16 to 18 cm.
2. The lower leaves are primarily green in color and provide excellent contrast with the sturdy flower cone.
3. The inflorescence is long lasting.
4. The leaf sheaths are well formed and closely linked at the base. The sheaths have a green color, without a distinct stripy pattern of another color. The oldest leaves are spatulate; the new ones are linear and they have a pointed tip. The leaf edge is entire and the leaf blade is ribbed.

The accompanying photographic drawings show the inflorescence and foliage characteristics of Triumph as clearly as possible. The photo on the first sheet comprises a top perspective view of a plant of Triumph in bloom. The photo on the second sheet comprises an enlarged top perspective view showing the inflorescence in more detail. The colors are as nearly true as possible with illustrations of this type.

Triumph can be compared in certain respects to the commercially available Guzmania 'Denise'. Triumph is similar to Denise with respect to size and color of green foliage. Triumph is distinguished from Denise by its bright red short bracts that extend to the heart of the plant, and its thicker and shorter flower stem.

In the following description, color references are made to The Royal Horticultural Society Color Chart. The color values were determined at Laarne, Belgium.

Classification:

*Botanical*.—Guzmania squarrosa×minor hybrid. cv. Triumph.

PLANT

Form: Rosette.

Height: Approximately 39 cm when plant is in bloom. The leaf rosette has a height of approximately 23 cm.

Diameter: Approximately 65 cm when plant is in bloom.

Growth habit: Short stem.

Method of propagation: By offshoots or tissue culture.

Foliage:

*Quantity.*—Rosette is comprised of approximately 23 leaves having a length from 40 to 45 cm, forming a close rosette of which the bottom leaves are much shorter (12 cm) than the new ones formed.

*Size.*—Bottom leaves have width of 3.3 to 4.3 cm and top leaves have a width of about 6.0 cm. Length varies as noted above.

*Shape.*—Oldest leaves are spatulate; new leaves are linear with a pointed tip; leaf edge is entire.

*Surface texture.*—Slightly ribbed, both top and bottom surfaces.

*Color.*—The top surface is approximately 137A and the bottom surface approximately 137B.

*Leaf sheaths.*—Well formed and closely linked at the base, having a length of about 8 to 11 cm for the bottom leaves and 11 to 13 cm for the top leaves. Color is approximately 137B, without variegation or stripy pattern of another color. The edges are fleshy and sinuate.

BRACTS

Quantity: Approximately 25 in number, with the base of the bracts completely surrounding the flower shaft.

Size: Bracts at bottom of the flower shaft are approximately 16 to 18 cm in length and 4 to 5 cm in width; bracts near top of flower shaft have a length of about 10 cm and a width of about 7.5 cm.

Shape: The compound flower system constitutes a cone.

Color: The bracts are 42A in color when the plant is in bloom, later fading slightly to 43A-B, with the lower bracts having green tips as shown in the photo on sheet 2.

FLOWERS

Borne: Approximately 9 head-like subflower systems, a term used to collectively designate the bracts of the individual flowers, are each separately embedded in the axils of one of the top bracts. Individual flowers cling to a fibrous receptacle.

Blooming habit: Flowers bloom approximately 16 weeks after induction. Single flowers bloom only one day, inside the subflower system, and total inflorescence (from first to last flower) lasts approximately eight (8) weeks. After blooming, the subflower system gets more pronounced.

Quantity: 15 single flowers in each subflower system.

Size: The entire flower system has a length of approximately 8 cm and a diameter of 6 to 8 cm. The subflower systems have a length of 5 cm and a diameter of 3 cm. Each individual flower is about 4 cm in length.

Shape: The subflower systems are sloping out of the axils of the top bracts. The flower grows straight in the subflower system.

Color: The bract of each flower is transparent 50A-B to a transparent white.

Sepals: Are fasciated up to one third of their length, and are transparent with white stripes; they have a length of 3 cm and a width of 6 mm.

Petals: Are fasciated up to two thirds of their length; color 7A-B, length about 3–4 cm.

Reproductive Organs: The 6 stamens are fasciated similar to the corolla; the anther has a length of about 7 mm and the filament has the length of about 2.5 cm. The pistil has a length of 4 cm when ripened and it bears 3 stigmas.

I claim:

1. A new and distinct cultivar of Guzmania plant named Triumph, as illustrated and described.

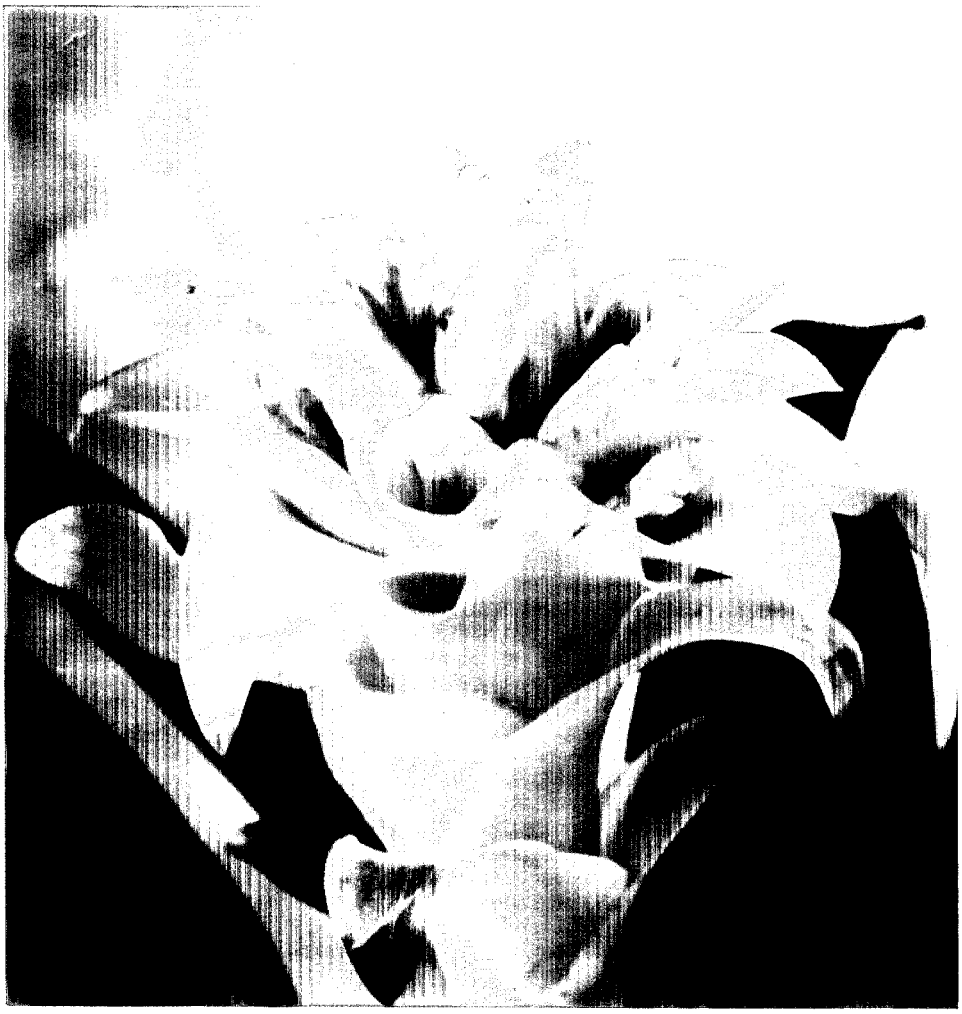

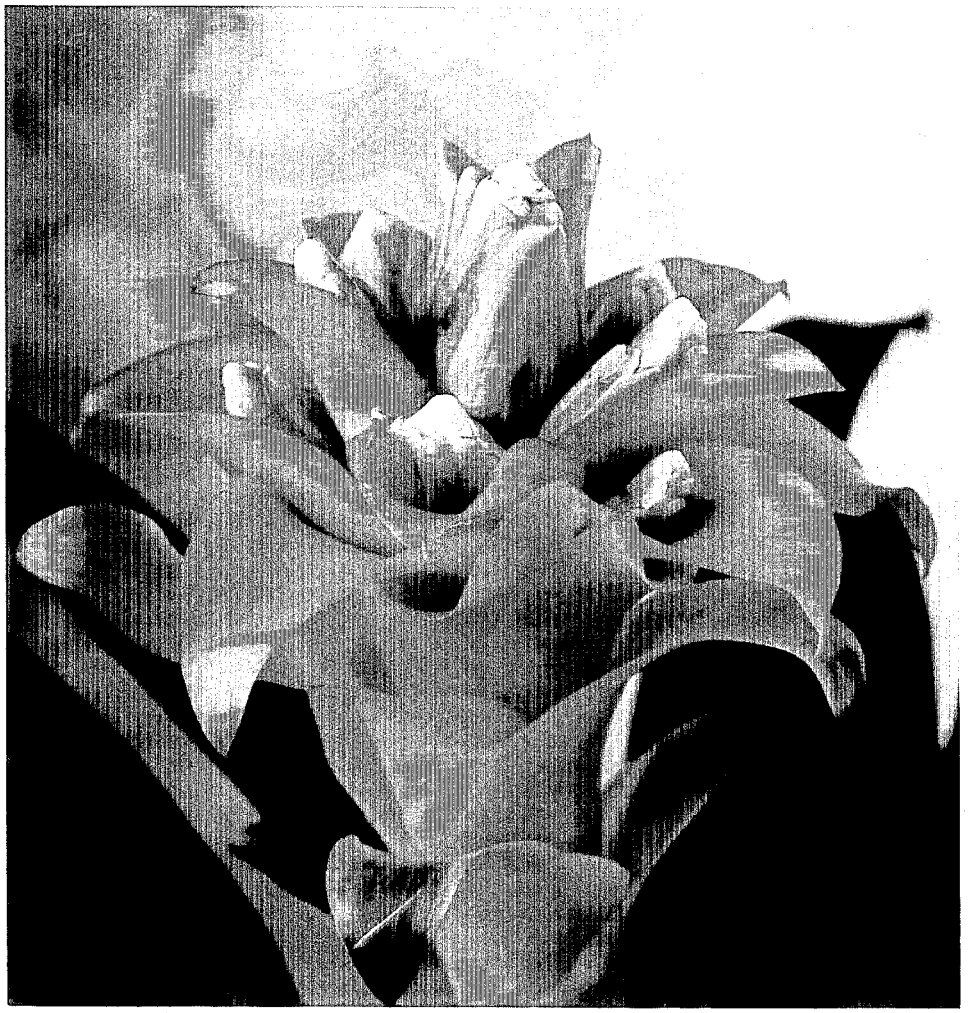

* * * * *